United States Patent [19]

Markovic et al.

[11] Patent Number: 5,358,855

[45] Date of Patent: Oct. 25, 1994

[54] INOSINIC ACID DEHYDROGENASE ASSAY

[75] Inventors: Olivera T. Markovic, Philadelphia, Pa.; Nenad S. Markovic, Novi Sad, Yugoslavia; Jay Roberts, Rosemont, Pa.; Charles D. Puglia, Glenside, Pa.; Svetomir N. Markovic, Philadelphia, Pa.

[73] Assignee: The Medical College of Pennsylvania, Philadelphia, Pa.

[21] Appl. No.: 882,647

[22] Filed: May 14, 1992

[51] Int. Cl.$^5$ .............................................. C12Q 1/32
[52] U.S. Cl. .................................... 435/26; 435/29; 435/34; 435/975; 436/64; 436/166
[58] Field of Search ............... 435/26, 29, 975, 34, 435/7.23; 436/64, 166

[56] References Cited

U.S. PATENT DOCUMENTS

| | | | |
|---|---|---|---|
| 3,925,154 | 12/1975 | Enei et al. | 435/92 X |
| 4,254,222 | 3/1981 | Owen | 435/26 |
| 4,351,899 | 9/1982 | Owen | 435/26 |
| 4,427,771 | 1/1984 | Misaki et al. | 435/22 |
| 4,629,697 | 12/1986 | Limbach et al. | 435/26 |
| 4,683,198 | 7/1987 | Ishikawa et al. | 435/22 |
| 4,849,347 | 7/1989 | Familletti et al. | 435/26 |
| 4,916,061 | 4/1990 | Di Ianni | 435/34 |
| 5,036,000 | 7/1991 | Palmer et al. | 435/26 |

OTHER PUBLICATIONS

Negishi et al., Reagent for spectrometric determination of inosinic acid, Japan, Kokai Tokkyo Koho, 12 pp., Oct. 12, 1989, Heisei.

Henderson et al., Inhibitors of Inosinate dehydrogenase activity prog. chemother, proc., Int. Congr. chemother., 8th Meeting Date 1973, vol. 3, 152–4.

Jayaram, Cytotoxicity of New IMP dehydrogenase, Biochem. Biophys. Res. Commun., 186(3), 1600–6, 1992.

Yamada et al., Two distinct target sites on IMP dehydrogenase Adv. Exp. Med. Biol., 253B (Purine Pyrimidine Metab. Mang. Pt. B).

*Primary Examiner*—James C. Housel
*Assistant Examiner*—Harold Y. Pyon
*Attorney, Agent, or Firm*—Webb Ziesenheim Bruening Logsdon Orkin & Hanson

[57] ABSTRACT

A cyto(histo)chemical technique for determining inosine 5'-monophosphate dehydrogenase (IMPD) presence and concentration within one or more morphologically classified or classifiable cells taken from an animal or a human subject. Cell monolayers are prepared, fixed and stained according to a specified procedure in which inosine 5'-monophosphate (as enzyme substrate), nicotinamide adenine dinucleotide (NAD), phenazine methosulfate (PMS) and nitro blue tetrazolium (NBT) as a diazonium salt together produce a granular, dark blue deposit of formazan generally proportional to the IMPD activity in the cell. Cells are evaluated either visually or by image analysis, with a computerized image analyzer or other imaging system, according to accepted biostatistical methods and standards.

6 Claims, No Drawings

INOSINIC ACID DEHYDROGENASE ASSAY

FIELD OF THE INVENTION

The present invention relates to an assay for measuring inosinic acid dehydrogenase activity inside one or more individual morphologically classified cells.

BACKGROUND OF THE INVENTION

The increased activity in cancer cells of inosine 5'-monophosphate dehydrogenase (IMPD) or inosinic acid dehydrogenases in general has led to the suggestion that inosinic acid dehydrogenases be used as a sensitive target for chemotherapy. Inosine 5'-monophosphate dehydrogenase is the rate-limiting enzyme of de novo guanosine 5'-triphosphate (GTP) biosynthesis, with GPT playing a key role in polypeptide chain activation during protein synthesis and other vital anabolic biochemical processes. Various inhibitors of IMPD have been used as cancer chemotherapeutic treatments, therefore, including tiazofurin (NSC 286193, 2-beta-D-ribofuranosylthiazole-4-carboxamide) and mycophenolic acid. In some clinical trials, tiazofurin (through its metabolic conversion to the active metabolite thiazole-4-carboxamide adenine dinucleotide (TAD)) caused return to a chronic phase in patients with chronic granulocytic leukemia in blast crisis. Mycophenolic acid and retinoic acid have been documented as inducing maturation of malignant cells. Tiazofurin was found to be a highly effective inhibiting agent of solid tumor metastasis in mice. Other efforts are ongoing in the investigation of the efficacy of IMPD inhibitors in the treatment of various tumors, and these efforts are generally regarded as effective and/or promising.

To the extent that IMPD-inhibitors continue to be indicated and prescribed to combat neoplasms exhibiting elevated IMPD levels, health care providers have need of a reliable and relatively simple diagnostic assay for IMPD. Previous assays for IMPD have primarily if not exclusively involved biochemical analysis of tissue homogenates, but such assays have serious drawbacks. For one thing, in a given tumor biopsy both tumor cells and nontumor cells (lymphocytes, for example, and other immune and non-immune cells) are present. An assay of a homogenate of these tumor and nontumor cells will not indicate the IMPD level in the tumor cells alone but in the homogenate as a whole—even though it is an elevated IMPD level in the actual tumor cell which is predictive of successful IMPD-inhibitor treatment. A need therefore remains for an IMPD assay which can quantify IMPD within individual tumors or otherwise morphologically classified animal or human cells.

SUMMARY OF THE INVENTION

In order to meet this need, the present invention is a cyto(histo)chemical technique for determining IMPD presence and activity within one or more morphologically classified or classifiable animal or human cells. Cell monolayers are prepared, fixed and stained according to a specified procedure in which inosine 5'-monophosphate (as enzyme substrate), nicotinamide adenine dinucleotide (NAD), phenazine methosulfate (PMS) and nitro blue tetrazolium (NBT) salt together produce a granular, dark blue deposit of formazan. An optional counterstaining technique follows which permits confirmation of morphological classification. Cells are then evaluated with image analysis (image analyzers are well-known in the art) according to accepted biostatistical methods and standards, with the greater deposits of formazan indicating higher intracellular activity of IMPD. However, new processing parameters were included to report data in enzyme units.

DETAILED DESCRIPTION OF THE INVENTION

The present assay for IMPD is a cyto(histo)chemical technique which identifies and quantifies IMPD in individual, single-layer morphologically classified or classifiable cells. Cell monolayers derived from a tumor (i.e., suspected neoplasm) are prepared, fixed and stained according to a specified procedure in which inosine 5'-monophosphate, nicotinamide adenine dinucleotide (NAD), phenazine methosulfate (PMS) and nitro blue tetrazolium (NBT) salt together produce a granular, dark blue deposit of formazan. Morphological classification is accomplished with counterstaining. Cells are then evaluated with image analysis according to accepted biostatistical methods and standards, with the greater deposits of formazan indicating the higher concentrations of an active IMPD.

First, it is necessary to prepare microscope slides with a monolayer of single, well preserved cells amenable for cytochemical treatment and conventional staining to provide criteria for morphologic classification and measurement of intracellular enzyme activity.

Liquid tissues, blood and bone marrow provide natural suspension of cells ready for smearing. Tumor cells exfoliated into tissue liquors should be cytospinned (spinned by a Cytospin centrifuge, Shandon Co., Pittsburgh, Pa.) on microscope slides. Imprint techniques, usually used for preparation of single cell specimens from solid tumors, are less desirable than techniques for harvesting and culturing cells from a fresh tissue cut. Thin-needle biopsy material should be cultured in suitable cell growth medium prior to smearing. Blood and bone marrow cells, cell cultures and cell lines grown either in suspension or on slides present ideal single cell layer specimens.

The ideal fixation for the cell monolayers once formed is air drying, as chemical fixatives may affect enzyme activity. Air drying for five minutes is an appropriate minimum fixation.

An important aspect of the assay is the addition of inosine 5'-monophosphate (IMP) or other inosinic acid derivative to the cells as a substrate for the IMPD or other inosinic acid dehydrogenase. The assay is conducted with two controls: one control proceeds without NBT, to detect all nonspecific staining; the other control proceeds without the IMP to exhaust other cellular dehydrogenase-like reactions and to establish a threshold of detection for the sole activity of IMPD.

To demonstrate IMPD activity within individual cells we exposed cell smears for sixty minutes at 37 degrees C. to an incubation mixture containing IMP (substrate), NAD (enzyme cofactor), PMS (electron acceptor) and NBT as a diazonium salt that, after reduction, produces a granular dark blue deposit of formazan. The reagent for the first control described above-denoted as "Control-1"—contains all the reaction components except the IMP, and "Control-2" contains all reaction components except the NBT. Particular examples and exemplary complete formulas for Control-1, Control-2, and the Test formula containing all the reaction components with no omissions, appear in the Examples, below. The invention inheres primarily in the use of the identified reactants in an IMPD-identifying stain, however, and only peripherally resides in the specific reagents with respect to constituent amounts and other characteristics (buffering, pH, etc.).

It is believed, although the invention is not to be bound by this theory, that the following reactions occur during the incubation in order to yield the formazan precipitate which indicates IMPD concentration (after the "background" formazan precipitates occurring in the control slides is subtracted). Control-1:

X+NAD+PMS+NBT-
→NADH+PMSH+NBTH (formazan) Control-2:
IMP+NAD+PMS→IMPH[XMP]-
+NADH+PMSH Test:
IMP+NAD+PMS+NBT→IMPH[XMP]-
+NADH+PMSH +NBTH As can be seen from the above reactions, in the test slides formazan deposits will result in part from the activity of any IMPD present in the cells on the IMP substrate added by means of the test reagent. However, in the Control-1 slides formazan may also precipitate as a result of the activity of cellular dehydrogenases or dehydrogenase-like enzymes other than IMPD. The Control-1 cells therefore exhibit a background level of staining, or formazan precipitation, against which the formazan deposits of the test cells can be compared. Any staining which occurs in Control-2 cells represents nonspecific staining—if any—which should also be considered as a background level when the test cells are examined. In other words, some but not all of the formazan deposits in the test cells will be precipitated by the IMPD present in the test cells, but some of the formazan may also be precipitated by either other dehydrogenase-like enzymes or by general background staining, which can both be estimated and accounted for by examination of the two controls.

On the simplest level, the test cells and the two controls may be examined by a pathologist under optical microscopy. Standard microscopic techniques for morphologically classifying cells may be used, and then background and test staining (formazan deposits) can be compared in the test and control cells. In other words, pathologists are generally able to distinguish tumor cells from lymphocytes (etc.) in any given smear, and the formazan deposits should be analyzed and compared only as between the tumor cells. If great amounts of formazan deposits in the test tumor cells are present, as compared to the background staining in the Control-1 and Control-2 cells, this indicates high IMPD presence or activity in the tumor cells and confirms the susceptibility of the tumor cells to IMPD-inhibitory therapy. These observations can be extended, according to the amount of formazan present, to a somewhat more formal identification of four categories of cells: 1) negative (no formazan); 2) low IMPD activity (few granules visible); 3) intermediate IMPD activity (diffuse, scattered granules of formazan in cell) and 4) high IMPD activity (heavy granular deposit filling the entire cytoplasm and covering the nuclei of each cell in question).

Other morphological classification criteria known in the art include, for example, subclassification of different blast cell types in acute leukemia based on cytochemical criteria, cell line cells classification, mitotic stage, subcellular organelles and morphological integrity with other indicia of cell destruction.

On a more complex level, the test cells and the two controls may be examined by image analysis, with a computerized image analyzer known in the art. Generally speaking, an image analyzer conducts the same comparison described above but with quantification and statistical analysis more elaborate and precise than mere observation can accomplish. Because techniques for comparative evaluation of stained test and control cells are well-known in the image analysis field, no further description is needed here except to note that the image analysis is the only technique available to measure IMPD activity inside single cells in enzyme units. For less critical requirements even simple comparative methods (i.e., visual inspection) are effective in the determination of the high levels of formazan deposits which indicate high activity or concentration of IMPD in the cells in question.

The optional counterstaining techniques allow the pathologist to confirm morphological classification with counterstaining methods known in the art. If possible, morphological classification of cells is conducted without counterstaining, so that the counterstaining does not interfere with the stain comparison intrinsic in the analysis of the Test, Control-1 and Control-2 cells. However, when necessary, counterstaining techniques known in the art may be used to confirm morphological classification, and then the counterstaining should be taken into consideration when the formazan deposits are contrasted. Generally, when counterstaining is used the contrast between low-IMPD and high-IMPD cells will be less that the contrast which will be evident when counterstaining is not used. Those skilled in the arts of counterstaining and image analysis (which are both well established fields) will easily accommodate the present assay to either counterstained or non-counterstained cells.

With the invention having been generally described above, the invention will be even more readily understood upon consultation of the following Examples.

EXAMPLE 1

Control-1, Control-2 and Test reagents were prepared as follows:
Control-1:
    NAD: 5.0 mg/ml
    PMS: 2.0 mg/ml
    NBT: 0.5 mg/ml
    HEPES buffer: 0.1M, pH 7.0 q.s.
Control-2:
    IMP: 40.0 mg/ml
    NAD: 5.0 mg/ml
    PMS: 2.0 mg/ml
    HEPES buffer: 0.1M, pH 7.0 q.s.
Test:
    IMP: 40.0 mg/ml
    NAD: 5.0 mg/ml
    PMS: 2.0 mg/ml
    NBT: 0.5 mg/ml
    HEPES buffer: 0.1M, pH 7.0 q.s.

These reagents were then used as incubation mixtures for cell smears; aliquots of reagents sufficient to wet and completely to cover the cells were used, and excess reagent beyond such aliquots although not harmful was unnecessary.

EXAMPLE 2

Tumor tissue collected by thin-needle biopsy was cultured prior to preparation of cell monolayer smears on glass slides. Six smears were prepared. The smears were air-dried for up to ten minutes. Each smear was then covered with an aliquot of one of the three test reagents identified in Example 1, for a total of two Control-1 slides, two Control-2 slides and two Test slides. The slides were incubated at 37 degrees C. for one hour. After incubation was complete, the slides were examined for morphological classification of cells, and for degree of formazan deposit both by visual inspection and image analysis.

EXAMPLE 3

The image analysis according to Example 2 was conducted as follows except that cells harvested from a leukemia patient were substituted for the thin-needle biopsy cells. "Imagescan" software developed by Carl Zeiss, Inc., Thornwood, N.Y. (Copyright 1985) was used. This system defined features to be measured between two cursors on a grey level scale between 0 and 255, and separated from other features on the plane image by a variable frame projected separately onto the microscope monitor. Using this variable frame we segmented the final reaction product (formazan precipitate) and the rest of a single cell as two major features. We measured area (a), density (d) and integrated optical density (IOD) of these features on a cell by cell basis, using the number of 25 morphologically identical cells as a sample unit. In this software, area is defined as number of picture points inside a binary image region limited by perimeter or a projected variable frame, density as a mean optical density per unit of detected area, and integrated optical density as a multiple between area and density or total optical density of the detected area.

A competent hematologist/cytologist determines the percentage of IMPD positive cells among a single cell type (a morphological classification group). This is another parameter known in the art.

Using Imagescan software one can measure a, d and IOD of final reaction product—frp (formazan deposit), and cell (total cell image) separately. These six parameters: a-frp, d-frp, IOD-frp, a-cell, d-cell and IOD-cell, together with the percentage of positive cells (% C+) are used to calculate following derived parameters: SCEP—Single Cell Enzyme Product, MCEP—Mean Cellular Enzyme Product, SDCEP—Standard deviation of MCEP, SECEP—Standard error, PI—Positivity Index, and EU—Enzyme Unit.

$$SCEP[ctrl\text{-}1] = \frac{d\text{-}frp[ctrl\text{-}1] \times a\text{-}cell[ctrl\text{-}1]}{\text{mean } a\text{-}cell[ctrl\text{-}2]}$$

$$SCEP[test] = \frac{d\text{-}frp[test] \times a\text{-}cell[test]}{\text{mean } a\text{-}cell[ctrl\text{-}2]}$$

MCEP[ctrl-1] and MCEP[test] are mean values of N positive cells measured on Control-1 and test slides.

$$PI[test] = \% C+ \times MCEP[test]$$
$$PI[ctrl\text{-}1] = \% C+ \times MCEP[ctrl\text{-}1]$$
$$EU = \frac{PI[test]}{PI[ctrl\text{-}1]} - 1$$

One enzyme unit is defined as a specific activity of IMPD necessary to convert IMP in presence of NAD, PMS and NBT into intracellular formazan deposit twofold the amount developed by nonspecific dehydrogenase activity.

EXAMPLE 4

A population of K562 cell line cells was examined for IMPD content using the techniques described above. After image analysis, the Control-2 cells gave no staining, the Control-1 cells measured 1.0 enzyme units (EU) and therefore the Test cells, which measured 2.7 EU, included 1.7 EU attributable directly to the IMPD present.

EXAMPLE 5

Random specimens were collected from acute leukemia patients undergoing induction of remission therapy. The percentage of blasts among other peripheral blood leukocytes varied in relation to the response to therapy. Almost all blasts demonstrated at least some level of IMPD activity.

Although the invention has been described with particularity above, the invention is to be considered limited only insofar as it is set forth in the ensuing claims.

We claim:

1. A method for assaying inosinic acid dehydrogenase activity within a cell, comprising the steps of:
    a) obtaining a tissue sample containing at least one cell from biopsied animal or human tissue in which increased inosinic acid dehydrogenase activity is suspected;
    b) using said tissue sample to prepare at least one smear containing cells and morphologically classifying said cells;
    c) drying said smear in ambient air for at least five minutes;
    d) contacting said at least one smear with a reagent containing at least one inosinic acid derivative, nicotinamide adenine dinucleotide, PMS and NBT to produce, during incubation of said smear, a visible formazan precipitate indicative of inosinic acid dehydrogenase activity; and
    e) quantifying said formazan precipitate to confirm and to measure the level of inosinic acid dehydrogenase activity in at least one morphologically classified cell of said smear.

2. The method according to claim 1 wherein said tissue is used to prepare at least three smears, each smear further comprising a cell monolayer, wherein one of said smears is contacted with at least one inosinic acid derivative, nicotinamide adenine dinucleotide, PMS and NBT, wherein the second of said smears is contacted with nicotinamide adenine dinucleotide, PMS and NBT and wherein the third of said smears is contacted with at least one inosinic acid derivative, nicotinamide adenine dinucleotide, and PMS, prior to incubation of all three smears.

3. The method according to claim 1 in which said inosinic acid dehydrogenase is inosine 5'-monophosphate dehydrogenase and said inosinic acid derivative is inosine 5'-monophosphate.

4. The method according to claim 2 in which said three smears are examined as Test, First Control and Second Control smears, respectively, by examining said Test smear to determine the total level of non-specific dehydrogenase activity and IMPD, examining said First Control smear to determine the level of non-specific dehydrogenase activity alone and examining said Second Control smear to establish the level of stain artifact.

5. The method according to claim 1 wherein said morphological classification is accomplished with counterstaining.

6. The method according to claim 1 wherein said quantification is conducted as image analysis with an image analyzer and the processing parameters derived from measuring data and used for report of IMPD activity in enzyme units.

* * * * *